United States Patent [19]
Blaszynski et al.

[11] Patent Number: 5,860,935
[45] Date of Patent: Jan. 19, 1999

[54] GAME APPARATUS AND METHOD FOR MONITORING PSYCHO-PHYSIOLOGICAL RESPONSES TO QUESTIONS

[75] Inventors: John E. Blaszynski, St. Catharines; Daniel G. Tibbs, Niagara Falls, both of Canada

[73] Assignee: Novid Inc., Niagara Falls

[21] Appl. No.: 741,420

[22] Filed: Oct. 29, 1996

[51] Int. Cl.⁶ ........................ A63F 9/24
[52] U.S. Cl. ........................ 600/547; 273/460
[58] Field of Search .............. 273/460; 607/56; 364/410; 600/308, 309, 546, 547

[56] References Cited

U.S. PATENT DOCUMENTS

| | | |
|---|---|---|
| 3,648,686 | 3/1972 | Payne . |
| 3,841,316 | 10/1974 | Meyer . |
| 4,331,160 | 5/1982 | Zito, Sr. . |
| 4,358,118 | 11/1982 | Plapp . |
| 4,625,732 | 12/1986 | Kasa et al. .................. 128/670 |
| 4,812,126 | 3/1989 | Gilliksen .................... 434/238 |
| 4,813,419 | 3/1989 | McConnell .................... 607/56 |
| 5,016,213 | 5/1991 | Dilts et al. .................. 364/410 |
| 5,089,745 | 2/1992 | Iannini ........................ 315/76 |
| 5,209,494 | 5/1993 | Spector ...................... 273/460 |

FOREIGN PATENT DOCUMENTS

WO 93/02622  2/1993  WIPO .

*Primary Examiner*—George Manuel
*Attorney, Agent, or Firm*—Bereskin & Parr

[57] ABSTRACT

An electronic party game, comprising display cards for displaying questions to be asked to a player, and a response monitor for monitoring the player's psycho-physiological responses to the questions. The response monitor comprises a housing dimensioned to be fit into the palm of the player answering the questions, the housing having an outside top surface shaped to receive two extended fingers of the player, and a pair of electrodes extending through the top surface, each of the electrodes being positioned to contact one of the extended fingers near the tip thereof, bias means operatively coupled to an outside portion of the housing for selectively biasing the player's fingers against the electrodes, an electronic circuit located within the housing which generates an electric current from one electrode to the other through the player's fingers and a voltage signal correlatable with the change in resistance resulting from the player's response to the questions, and an indicator which generates a signal indicative of the changes in resistance. The subject monitor is capable of monitoring a user's psycho-physiological responses to hearing a pair of questions and determining whether the user's response to the first question is greater than the user's response to the second question.

14 Claims, 4 Drawing Sheets

GAME APPARATUS AND METHOD FOR MONITORING PSYCHO-PHYSIOLOGICAL RESPONSES TO QUESTIONS

BACKGROUND OF THE INVENTION

This invention relates to party games, and more particularly, to electronic party games and components thereof.

Board-games, card games and other party games have provided entertainment for groups of people for many years. A number of party games require individual players to answer questions. These answers in turn entertain the group. One such game, known as Scruples (trade mark), tests individual players with moral dilemmas. A disadvantage associated with this game is that a player may lie, in answering the moral question, and often it is difficult or impossible for the other players to detect the lie.

There exist a number of lie-detector devices which have been considered to be suitable for entertainment purposes. U.S. Pat. No. 3,648,686 discloses an instrument for measuring the galvanic skin response, which utilizes a bridge amplifier and relies upon a change in the audible frequency to signal an untruth, but this device has poor resolution. U.S. Pat. No. 3,841,316 discloses an apparatus for measuring the psychogalvanic reflex, which also uses a resistance bridge circuit, but this device is not practical, since the transistor meter combination required to make the circuit practical does not exist. U.S. Pat. No. 4,331,160 discloses a lie-detector apparatus which is an improvement over that disclosed in the above patents, because it provides a constant baseline, but it also uses a resistance bridge circuit which does not create a linear output. Furthermore, these prior art devices are not very reliable lie-detectors, because they do not take into account the fact that a particular person may have a relatively high response to every question, or a relatively low response to every question, regardless of whether a person is telling the truth.

There also exist highly sophisticated polygraph machines which calculate scores corresponding to the certainty of deceit, based upon complex measurements of various factors, but these machines are very expensive, and can only be used by trained operators.

There is accordingly a need for a relatively simple, inexpensive lie-detector apparatus, adapted for use as a component of a party game.

SUMMARY OF THE INVENTION

The present invention is directed towards apparatus for monitoring and comparing user psycho-physiological responses to questions. The apparatus comprises a housing shaped to fit into the palm of a hand of the user, having an outside top surface shaped to receive a pair of extended adjacent fingers, and a pair of spaced electrodes extending through the top surface, each electrode being positioned to contact one of the extended fingers, and bias means coupled to the housing for selectively biasing the user's fingers against the electrodes. Current generating means located within the housing is electrically coupled to the electrodes and generates an electrical current flow from one electrode through a section of the user's body to the other electrode and a corresponding voltage signal which is proportional to the resistance of the section of the user's body. Measuring means coupled to the current generating means measures differences in the voltage signal created when the user responds to a given question. Signal generation means responsive to the measuring means generates a signal to the user correlatable with the differences in the voltage signal.

The present invention is also directed to an electronic party game comprising display means for displaying questions to be asked to a player, and monitoring means for monitoring the player's psycho-physiological responses to the questions. The monitoring means comprises a housing dimensioned to be fit into the palm of the player answering the questions, the housing having an outside top surface shaped to receive two extended fingers of the player, and a pair of electrodes extending through the top surface, each of the electrodes being positioned to contact one of the extended fingers near the tip thereof, and bias means operatively coupled to an outside portion of the housing for selectively biasing the player's fingers against the electrodes. Circuit means located within the housing generates an electric current from one electrode to the other through a section of the player's body, which creates a measurable electric signal correlatable with the change in resistance resulting from the player's response to the questions. Signalling means generates a signal to the other players indicative of the changes in resistance.

The present invention is further directed to a method and apparatus for determining which of two questions generates a greater psycho-physiological response in a user hearing the questions. The method comprises the steps of contacting adjacent fingers of the user to spaced electrodes; applying a current across the electrodes and generating a measurable voltage signal related to the resistance of a section of the user's body extending between the electrodes; signalling when the user should be asked a first question and allotting a time interval for the user's response; detecting the change in voltage signal across the electrodes when the user responds to the first question during the first time interval; filtering out components of the voltage signal outside of a preselected frequency range; storing a first filtered voltage signal for the first time interval; signalling when the player should be asked a second question and allotting a second time interval for the user's response; detecting the change in voltage signal across the electrode when the user responds to the second question during the second time interval; filtering out components of the voltage signal outside of a preselected frequency range; measuring a second filtered voltage signal for the second time interval; comparing the first filtered voltage signal with the stored filtered voltage signal and generating a comparison signal indicative of which of the two signals is greater; and displaying to the user an indication of the comparison signal.

BRIEF DESCRIPTION OF THE DRAWINGS

The invention will now be described, by way of example only, with reference to the following drawings, in which.

DETAILED DESCRIPTION OF THE PREFERRED EMBODIMENT

Figure 1:
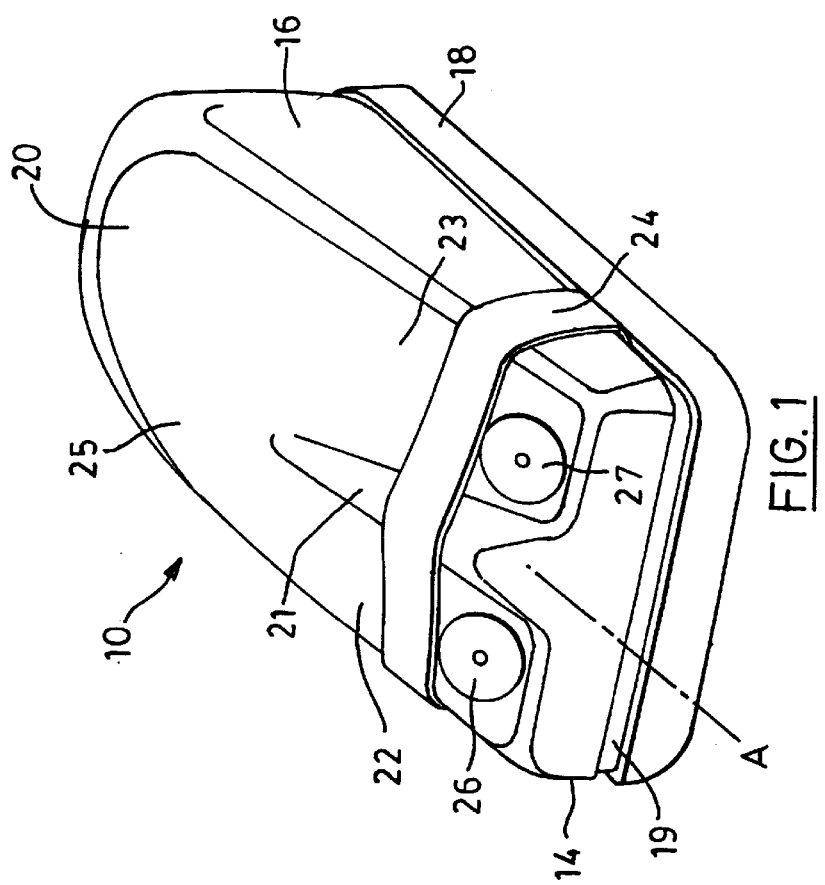
FIG. 1 is a perspective top view of a player response monitor of a party game made in accordance with the preferred embodiment of the subject invention.
Figure 2:
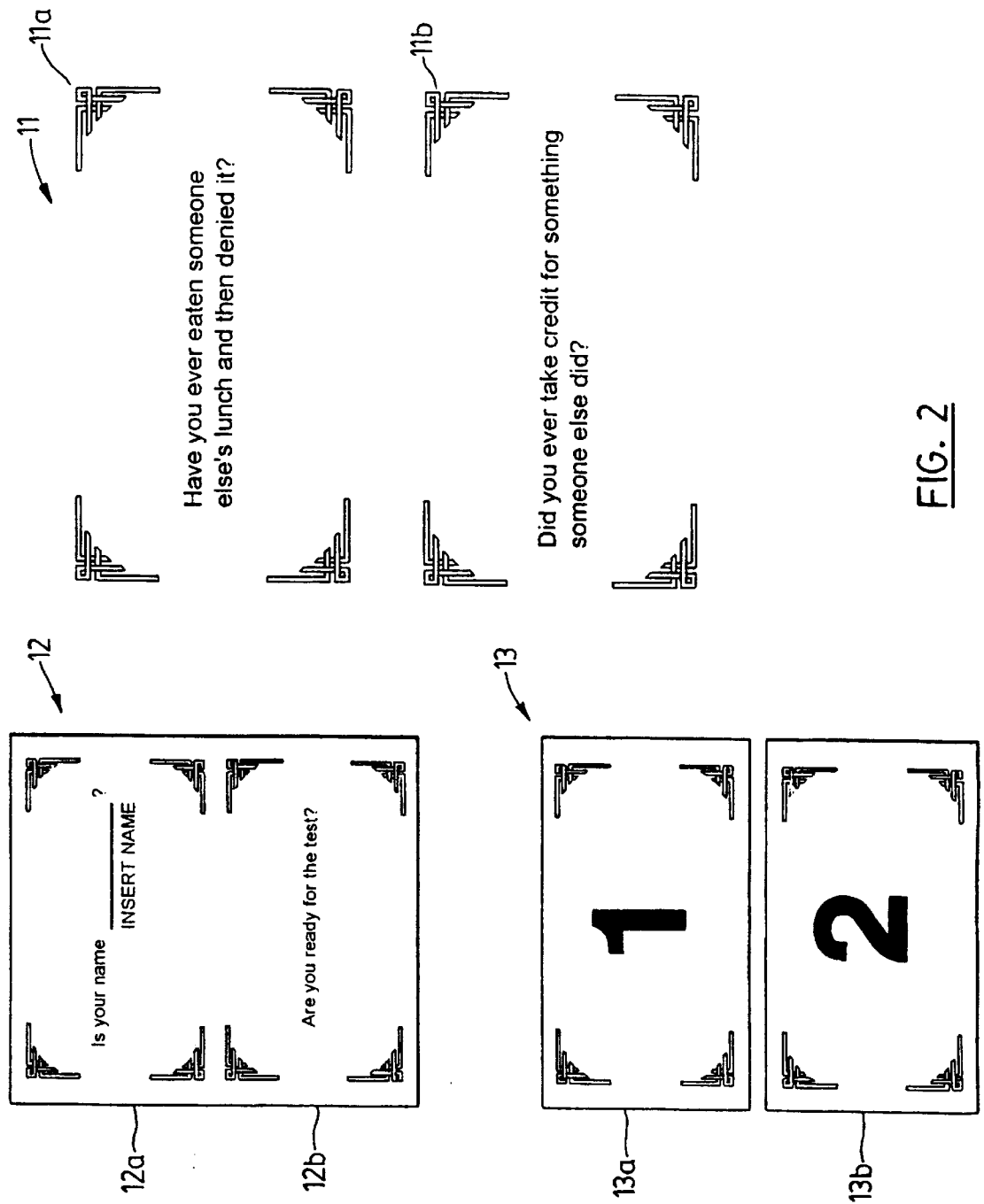
FIG. 2 is a schematic view of the display cards of the party game made in accordance with the preferred embodiment of the present invention.

Referring to FIGS. 1 and 2, a party game made in accordance with a preferred embodiment of the present invention comprises player response monitor 10 and a plurality of display cards 11, 12 and 13. Response monitor 10 is a portable, battery-powered device sized to fit into the palm of a user.

Each of question display cards 11a, 11b displays a different question designed to generate an emotional response. Control display card 12 is divided into two sections 12a and 12b, and displays questions designed to determine whether a player is calm enough to be asked a response question. Section 12a preferably displays the question "Is your name ?" and section 12b preferably displays the question "Are you ready for the test?". Indicator display cards 13a and 13b, marked "1" and "2" respectively enable the players asking the questions to indicate to the player being questioned which of the two questions they indicated would generate the greater emotional response, after the response is given. The subject party game preferably includes about 200 question cards like question cards 11a, 11b, each of which displays a different question.

Figure 3:
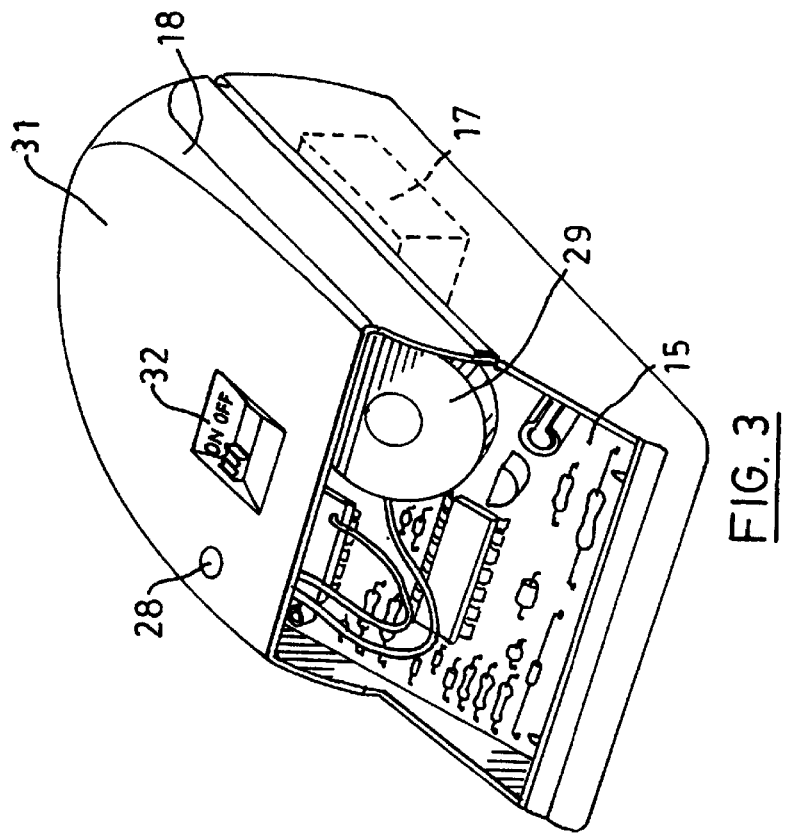
FIG. 3 is a partially cutaway perspective bottom view of the response monitor of the subject invention.

Referring now to FIGS. 1 and 3, response monitor 10 comprises a housing 14 shaped to be held comfortably in the palm of a user's hand, defining an interior space for accommodating printed circuit board 15 and battery 17. Housing 14 is composed of top housing portion 16 glued or otherwise joined to bottom housing portion 18 along junction line 19. Housing portions 16, 18 are preferably made of moulded plastic. Battery 17 is preferably a 9 volt transistor battery.

Top surface 20 of top housing portion 18 includes a longitudinal extending central divider ridge 21 which extends at a slight angle to the longitudinal axis A of housing 14, and divides top surface 20 roughly in half, to form index and middle finger rest areas 22, 23. Index finger rest area 22 is shaped to receive the index finger of a user's left hand and middle finger rest area 23 is shaped to receive the user's middle finger.

Spaced electrodes 26, 27 extend through and slightly above the top surface 20 in finger rest area 22, 23. Elastic band 24 protrudes outwardly from both sides of housing 14 along junction line 19, and extends over the top of spaced electrodes 26, 27 and divider ridge 21. Elastic band 24 acts as a biasing means to bias or urge the fingers of the user against electrodes 26, 27. Top surface 20 also includes openable battery compartment 25.

As shown in FIG. 3, light emitting diode (LED) 28 and speaker 29 extend through bottom surface 31 of bottom housing portion 18. LED 28 informs the question asker when to ask questions. Speaker 29 provides an audible sound, preferably either a long beep or a short beep. Bottom surface 31 is also provided with an on/off switch 32.

In the preferred embodiment, response monitor 10 compares the psycho-physiological responses of a user to two distinct questions. The first question is asked when LED 28 turns on, signalling the beginning of the first question period, and the second question is asked when LED 28 turns off after a preset time, signalling the beginning of the second question period. If the first question generates a higher response, speaker 29 will generate a short beep at the end of the second question period. If, however, response monitor 10 detects a higher response to the second question, speaker 29 will generate a long beep during the second question period. The audible beep is preferably a 400 Hz +/−100 Hz signal.

Figure 4:
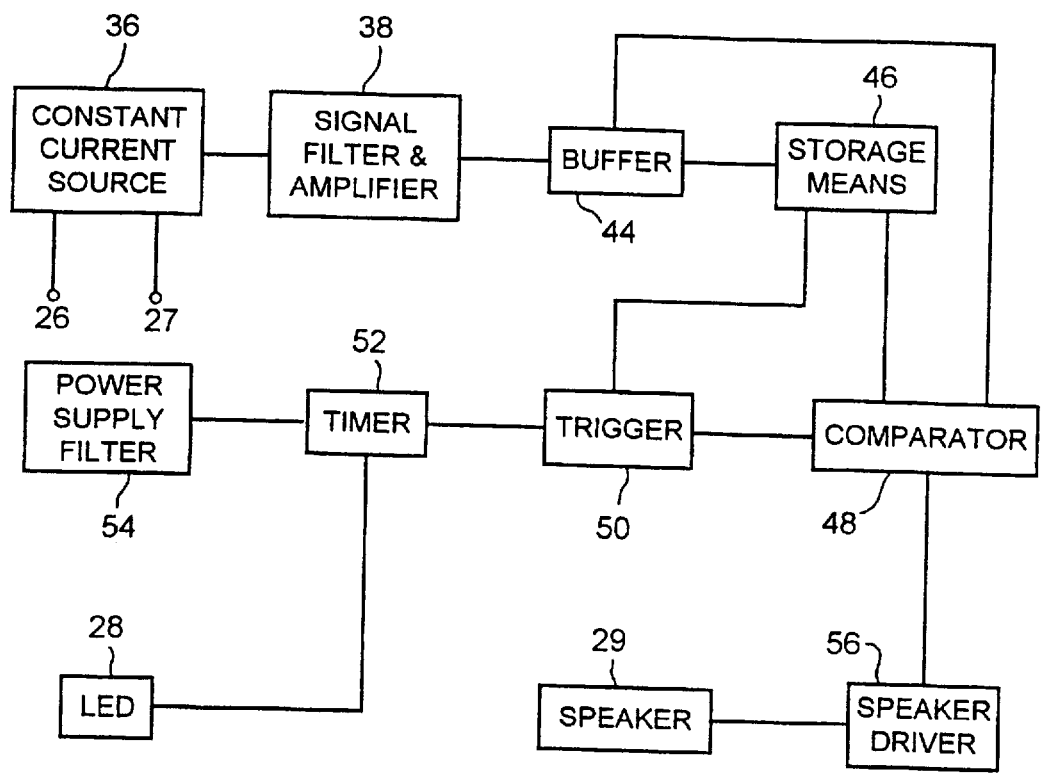
FIG. 4 is a block diagram of the electronic circuitry for the response monitor.
Figure 6:
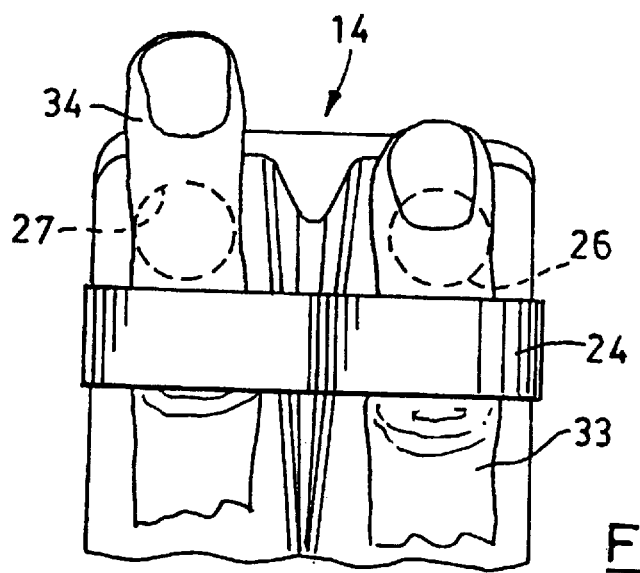
FIG. 6 is a top plan view of a portion of the response monitor in use.

Referring now to FIG. 4, the electronic circuitry of response monitor 10 comprises constant current source 36 coupled to electrodes 26, 27, signal filter and amplifier 38, buffer 44, storage means 46, comparator 48, trigger 50, timer 52, power supply filter 54 and speaker driver 56.

Constant circuit source 36 generates a constant current through a small section of the user's hand, extending across electrodes 26, 27. The current preferably ranges from about 2 microamps to about 7 microamps, depending upon the desired sensitivity and required range of human variability. Signal filter and amplifier 38 filters out undesirable signals outside of a preselected frequency range, preferably signals below about 0.1 Hz and above about 18 Hz, amplifies the desired response by about 1,000 times, or 60 dB, and provides a voltage signal which correlates to the user's response to hearing a question. Buffer 44 provides a small buffer against electronic noise. Storage means 46 clears the stored voltage signals at the beginning of the first question period, stores the voltage signal received during the first question, and stores the voltage signal received during the second question period. Comparator 48 compares the voltage signal generated by the second question to the voltage signal generated by the first question, and provides a signal out if the second question generates a higher signal. Comparator 48 also provides a signal out at the beginning of the questioning sequence. Trigger 50 provides a signal to clear the stored value in storage means 46 at the beginning of the question sequence. Timer 52 provides the timing for the entire circuit, including providing a signal to turn LED 28 on and off to indicate the questioning sequence, and a signal to comparator 48 to synchronize the clearing signal. Timer 52 also provides timing for storage means 46. The duration of the timing signal is preferably 8–15 seconds on, and 8–15 seconds off. Power supply filter 54 filters out any power supply noise. Speaker driver 56 includes an oscillator for speaker 29, and provides a signal to determine the length of the sound generated by speaker 29.

Figure 5:
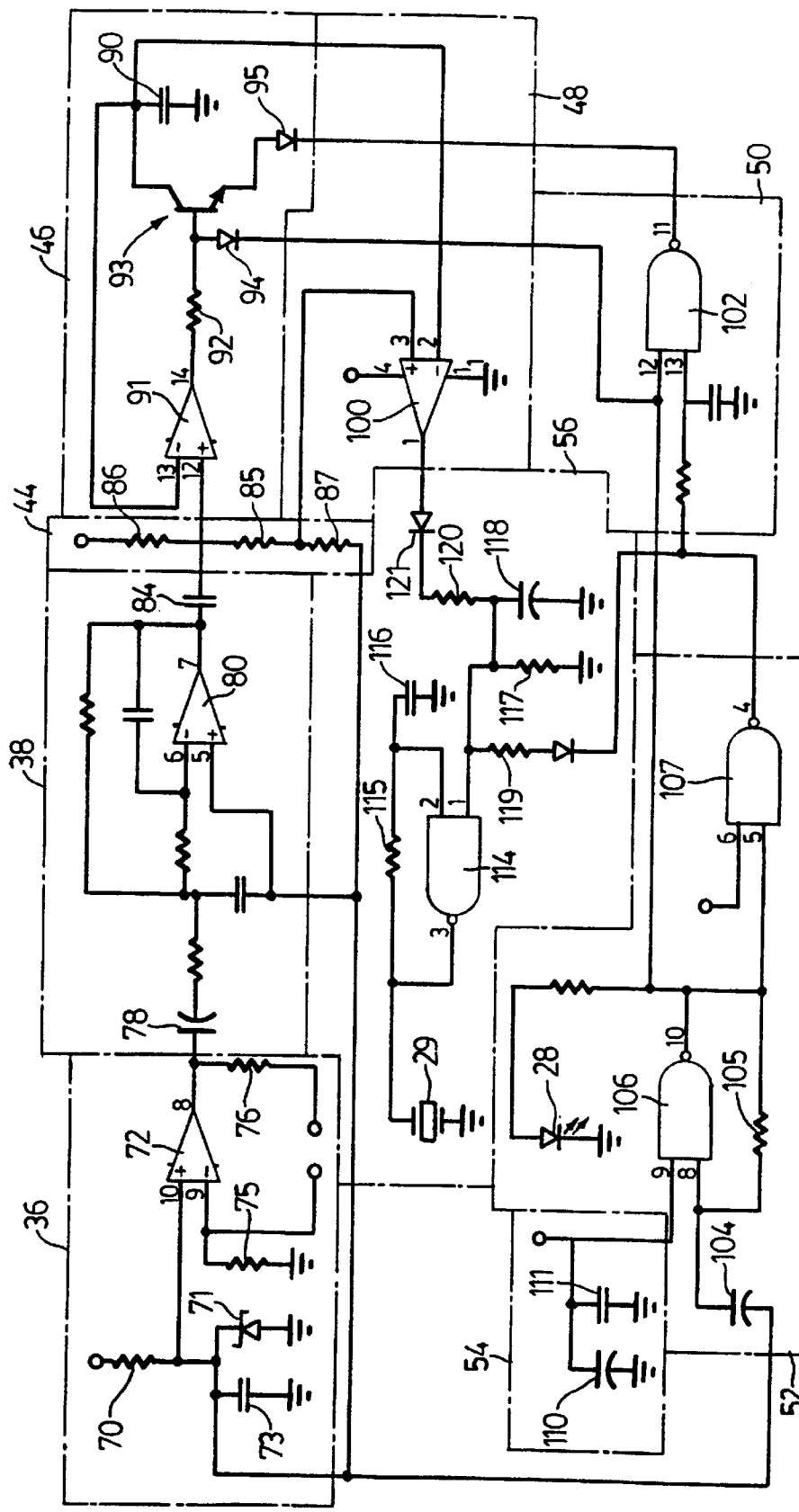
FIG. 5 is an electrical schematic diagram for the response monitor.

Referring now to the circuit diagram shown in FIG. 5, resistor 70 and zener diode 71 of constant current source 36 provide a constant voltage V to the non-inverting output of Op Amp 72. The voltage is preferably 3.2 volts+/± 5%. Capacitor 73 is used to filter out noise. Resistor 75 is connected to the inverting input of Op Amp 72, and is used to determine the value of a current which will travel through the hand of the person being questioned, which is determined by the equation: Current=3.2 Volts/R, where R is the resistance of resistor 75. The value of resistor 75 is preferably 1 megohm, which results in a 3.2 microamp constant current, giving an operational range of equivalent resistance of the user's body of from about zero to about 1.5 megohms. Resistor 76 protects the circuit. The output of Op Amp 72 provides a voltage proportional to the equivalent resistance of the body of the person being monitored by response monitor 10. The output of Op Amp 72 changes with corresponding changes in the equivalent resistance of the body.

Capacitor 78 and the Thevenin resistance of signal filter and amplifier 38, combine to filter out the changes in body resistance generated by movement and the user's overall level of relaxation or anxiety, and act as a DC shift or level adjustment. Op Amp 80 and related circuitry of signal filter and amplifier 38 provide a gain to the signal generated by the user when telling a lie, which has predominately 1–3 Hz frequency components. Capacitor 84 also filters out frequency components outside this desired frequency range.

Resistors 85, 86 and 87 of buffer 44 combine to give a reference voltage for storage means 46, and resistor 85 provides a buffer against noise into comparator 48.

Capacitor 90 of storage means 46 is connected to the output of Op Amp 91 through resistor 92 and the low leakage base connector diode of transistor 93. This part of storage means 46 functions as a peak detector, which saves the peak value of the response to question 1 as a voltage on capacitor 90. Resistor 92 is used to limit current through the small base collector junction. Transistor 93 and resistor 92 combine to clear the value stored on capacitor 90 at the end of question 2. The base-collection junction of transistor 93 functions as a low leakage diode, whereas the collector-emitter junction of transistor 93 functions as a transistor. Diode 94 and resistor 92 combine to prevent capacitor 84 from sampling the response to question 2. Capacitor 90 is used to hold the value of question 1 during question 2. Diode 94 and diode 95 are used in conjunction with the control signals from trigger 50 to program the clearing function, the peak detection function, and the hold function.

Op Amp 100 of comparator 48 is used in the open loop configuration as a comparator. It compares the level stored on capacitor 90 and connected to the inverting input of Op Amp 100, with the magnitude of the response to question 2, which is connected to the non-inverting input of Op Amp 100. The output of Op Amp 100 sends a logic high to speaker driver 56 when the second response is greater than the first response, thereby indicating a lie.

Trigger 50 comprises a NAND Gate 102, acting as a Schmitt trigger, which generates a 50 millisecond pulse low to clear capacitor 90 in storage means 46. NAND Gate 102 also causes comparator 48 (through storage means 46) to generate a short logic high at the beginning of question 1. The result is a short beep, which tells the operator to begin the questioning sequence.

Capacitor 104 and resistor 105 of timer 52 combine to control the timing for the circuit. NAND Gate 106 is configured as an oscillator using the RC timing constant and the hysteresis of the NAND Gate. The value of resistor 105 and capacitor 104 depend upon the amount of time required for the questioning and manufacturers' process variations. NAND Gate 107 is used as an inverter to condition control signals. LED 28 are used to indicate to the user when to ask the questions.

Capacitors 110 and 111 of power supply filter 54 are used to filter out noise induced on the power supply. Internal factors as well as noise generated by appliances and lighting are filtered out, although these problems are drastically reduced in any event due to the low power requirements of the circuit, and the elimination of an AC/DC power supply and noise with the use of a battery.

NAND Gate 114 of speaker driver 56 is used as an oscillator to drive speaker 29, which is preferably a piezo electric speaker. Resistor 115 and capacitor 116 are used to program the frequency of the output of speaker 29. Preferably, 400 Hz square wave is output to the speaker. Pin 1 of NAND Gate 114 is used as the control for the oscillator. A logic high turns it on and logic low turns it off. Resistor 117 and capacitor 118 combine to give a 4–5 second logic high to the speaker driver, to indicate a lie. Resistor 119 with the appropriate control signal provides a 0.2–0.3 second pulse to the speaker driver, to indicate the beginning of the question sequence with a short beep. Resistor 120 and diode 121 are used to start the time sequences, and resistor 120 also reduces false triggers and switching noise induced back into the power supply.

In use, referring now to FIG. 1, response monitor 10 is preferably placed in a user's left hand, such that user's index finger 33 and middle finger 34 make good contact with electrodes 26, 27. Elastic band 24 is then placed over the two fingers, thereby pressing the fingers 33, 34 against electrodes 26, 27. The middle finger of the user may extend over the front end of housing 14, as shown. The user should then turn his left hand palm up, so that LED 28 may be seen by person asking the questions.

The party game of the present invention may be played in accordance with the following rules:

1. Divide the players into two teams and determine who will begin the first session.
2. Turn on response monitor 10 and place it in the left hand of the first person to be questioned. (See diagram 1).
3. The person being questioned will now select two question display cards 11 randomly from the deck of question cards and must read the two questions to everyone playing the game.
4. The other team must now discuss which question will cause the highest emotional response from the player being questioned and place the corresponding indicator display card 13a or 13b face down in front of them.
5. No one is allowed to speak or make any noises during the questioning sequence and the person being questioned should close their eyes sit comfortably with both feet flat on the floor and the device facing up on their lap. When the START light comes on a short beep is heard. The following sequence must be followed and the person being questioned must respond with a YES or a NO only Repeat a and b up to three time if necessary. (See hints)
    a) START light ON "is your name . . . ?"
    b) START light OFF "Are you ready for the test?"
    c) START light ON Ask question number one.
    d) START light OFF Ask question number two.
6. A LONG BEEP indicates the second question caused the highest response. A SHORT BEEP indicates the first question caused the highest response. Turn up the indicator display card. A correct match scores one point for the team asking the questions. (The players might want to discuss the results at this point.)
7. Response monitor 10 is then connected to a person on the other team following the above procedure. Every person will eventually be connected to monitor 10.

There are three methods of play:

1. The game can be played to a final point value. A typical game played to ten will last about two hours.
2. The game can also be played to a time limit. The team with the most points after two hours wins.
3. You can also play just for the fun of it, utilizing response monitor 10 as a lie-detector. Ask any questions you want, one victim at a time, as discussed in more detail hereinbelow.

Hints:

If possible, place people with a knowledge of each other (i.e. spouses or close friends) on opposing teams. Attempt to have an equal number of males and females on each team. Women tend to be three to four times better at playing the subject game than men. In general, people tend to guess which question will generate the highest response only about a third of the time, so don't be discouraged if at first you don't do well.

Try to relax if you are going to be questioned. Take several deep breaths, relax and try to get as comfortable as possible. When being questioned, breathe normally and remain still. If the person being questioned has a response (a long beep) to question b) "Are you ready for the test?", repeat questions a and b. You can decide how many times to repeat the sequence to allow the person to relax. A person who is unable to relax will continually respond and will appear to have the highest response to the second question.

Wash your hands prior to the game. If your hands are extremely dry, use a small amount of hand cream.

When determining which question will give the highest emotional response, consider the following. If the question will cause embarrassment, humour, guilt, anger, disgust, or sexually stimulate the person, a high response will be measured even if the person is not lying. The other players in the game will also affect the responses to questions. For example, a question regarding citizenship of your country is unlikely to cause much of a reaction for most people, however if you were to ask this question to an illegal alien with an immigration worker in the room the response would be quite different.

If you have knowledge of an incident which relates to a question, you can use this to your advantage. If you feel, the person will respond highly to that question you can increase the response by subtly reminding them of the incident. Attempt to determine the person's reaction when the questions are first being read.

The game includes three extra cards. The indicator two cards 13a, 13b have either the number 1 or number 2 on them and are used to secretly pick the number of the question which you think will give the highest response. The other card is a double control card 12 which has the questions "a) is your name . . . ?" and b) Are you ready for the test?" These form part of the questioning sequence. You can place them in order with the two question cards 11 to make it easier to ask the questions (i.e. a,b,c,d) See rule 5 and/or diagram 2.

The response monitor 10 of the subject invention may be used as a lie-detector for entertainment purposes, keeping in mind that the reliability of a lie-detector depends greatly on the skill and training of the person asking the questions. It should also be appreciated that the psycho-physiological response created by a lie is very similar to embarrassment, sexual arousal, anger, disgust or humour.

Therefore, when formulating the questions, the user must be very careful that the response is generated by the lie and not other emotions. The setting is important as well. The room should be quiet and free from distractions. It is recommended that the person being questioned close their eyes. The person being questioned must be familiar with the sequence of questions to follow and be prepared. When asking the questions, it is important to watch the person's breathing. The person must maintain normal breathing through the entire test or they may alter the results. A small wager on the results may improve the results.

| a) | START light ON | "Is your name . . . . . . . . . . . . . ?" (insert person's name) |
|----|----------------|------------------------------------------------|
| b) | START light OFF | "Are you ready for the test?" |
| c) | START light ON | "Is your name . . . . . . . . . . . . . ?" (insert person's name) |
| d) | START light OFF | Ask a relative question |

When asking questions a) and c) the person being questioned must respond NO. This is called a directed lie. The questioner knows the person's name and instructs the person to lie about it. The "Lie Detector" then compares this response to the response measured when question d) is asked. Question d) must be phrased so the response to the question is NO (i.e. Did you steal a cookie from the cookie jar today?). The questions must be specific to avoid a misunderstanding. Most of the questions supplied with the game are examples of poor "lie detector" questions. The questions in the game were designed to be open ended or have many interpretations. This is designed to increase the enjoyment of the game and illustrate how poorly people tend to understand their friends and relatives, but gives very little insight into the truthfulness of the response. This is because it is not certain what generated the response.

If the person has a response to question b) the questioner should repeat questions a) and b) until no response is registered. If the person has a response to this questions (LONG BEEP) they are not ready for the test. This could mean they already know they are going to fail or they are not sufficiently relaxed to get accurate readings. A LONG BEEP after question d) is a good indication that the person is being deceitful. Repeating the test several times can increase the reliability.

Response monitor 10 of the subject invention provides a number of advantages over known lie-detector game devices. Response monitor 10 compares the magnitude of the response to a relative question (a second question), to the magnitude of a directed lie (the first question). The subject response monitor may also function as an emotional response monitor, which compares the emotional responses to two different questions.

The subject response monitor effectively filters out signals not due to the lie or emotional response, and being hand-held without any long wires, it is less sensitive to radio frequency and other electrical noise, and less susceptible to contact variation.

Unlike sophisticated polygraph systems used by police forces, the subject response monitor can be used by lay persons not trained in polygraph operation. The subject response monitor is much smaller and more transportable than professional polygraph machines. The subject device is also more comfortable to use, and far less expensive than professional lie-detector machines, which typically sell for several thousands of dollars.

It should be understood that various modifications can be made to the preferred embodiment described and illustrated herein, without departing from the subject invention, the scope of which is defined in the appended claims.

We claim:

1. Hand-held apparatus for monitoring a user's psycho-physiological responses to questions, comprising:
   (a) a housing shaped to fit into the palm of a hand of the user, having an outside top surface shaped to receive a pair of extended adjacent fingers, and a pair of spaced electrodes extending through the top surface, each electrode being positioned to contact one of the extended fingers;
   (b) bias means coupled to the housing for selectively biasing the user's fingers against the electrodes;
   (c) current generating means located within the housing and electrically coupled to the electrodes for generating an electrical current flow from one electrode through a section of the user's body to the other electrode and a corresponding voltage signal which is proportional to the resistance of the said section of the user's body;
   (d) measuring means located within the housing and coupled to the current generating means for measuring differences in the voltage signal created when the user responds to a given question; and
   (e) signal generation means located on an outside portion of the housing responsive to the measuring means for generating a signal to the user correlatable with the differences in the voltage signal.

2. The apparatus defined in claim 1, wherein the measuring means comprises filtering means for filtering out changes in the voltage signal having frequency components outside of a preset frequency range and generating filtered voltage signals, and comparing means for comparing the values of successive filtered voltage signals and generating an output signal indicator of the said values.

3. The apparatus defined in claim 2, wherein the current generating means generates a constant current through the said section of the user's body.

4. The apparatus defined in claim 2, wherein the preset frequency range extends from about 0.1 Hz to about 18 Hz.

5. The apparatus defined in claim 1, wherein the top outside surface of the housing comprises a ridge extending between the spaced electrodes.

6. The apparatus defined in claim 1, wherein the bias means comprises an elastic band which simultaneously biases each of the extended fingers against one of the pair of electrodes.

7. An electronic party game, comprising:
  (a) display means for displaying questions to be asked to a player by other players; and
  (b) hand-held monitoring means for monitoring the player's psycho-physiological responses to the questions, said monitoring means comprising:
    (i) a housing dimensioned to be fit into the palm of the player answering the questions, said housing having an outside top surface shaped to receive two extended fingers of the player, and a pair of electrodes extending through the top surface, each of the electrodes being positioned to contact one of the extended fingers near the tip thereof;
    (ii) bias means operatively coupled to an outside portion of the housing for selectively biasing the player's fingers against the electrodes;
    (iii) circuit means located within the housing for generating an electric current from one electrode through a section of the player's body to the other electrode and for generating a measurable electric signal correlatable with the change in resistance in the said section of the player's body resulting from the player's response to the questions; and
    (iv) signalling means located on an outside portion of the housing for generating a signal to the other players indicative of the changes in resistance.

8. The electronic party game defined in claim 7, wherein the circuit means also comprises:
  (a) filtering means for filtering out components of the measurable electric signal outside of a preselected frequency range and generating a filtered signal;
  (b) measuring means for measuring the magnitude of the filtered signal; and
  (c) comparator means for comparing the magnitude of successive filtered signals and determining which is larger.

9. The electronic party game defined in claim 8, wherein the display means comprises a plurality of cards, said cards each displaying a different question designed to elicit an emotional response.

10. The electronic party game defined in claim 9, wherein the display means also comprises a control card displaying questions designed to determine whether a player is ready to be asked a question.

11. The electronic party game defined in claim 10, wherein the display means also comprises indicator cards displaying an indicator of which question the other player believes would generate the larger signal.

12. The apparatus defined in claim 11, wherein the measuring and storage means comprises a transistor having a base-collector junction functioning as a low leakage diode, while said transistor also functions as a switching device.

13. A hand-held apparatus for monitoring a user's psycho-physiological responses to hearing a pair of questions and determining whether the user's response to the first question is greater than the user's response to the second question, comprising:
  (a) a housing having a surface provided with a pair of electrodes, each electrode being positioned to contact one of the user's fingers;
  (b) current means located within the housing for applying a current across a small section of the user's hand between the two electrodes and generating a corresponding voltage signal which is proportional to the resistance sensed between the two electrodes;
  (c) filtering means located within the housing coupled to the current means for filtering out voltage signals of frequencies outside of a preselected frequency range and generating a filtered voltage signal;
  (d) signalling means located within the housing for signalling when a user should be asked a first question and allotting a time interval for receiving the user's response;
  (e) measuring and storage means located within the housing and coupled to the filtering means for measuring a first change in the filtered voltage signal when the user responds to the first question during the first time interval and storing the first change in filtered voltage signal;
  (f) signalling means located on a portion of the outside surface of the housing for signalling when a player should be asked the second question and allotting a time interval for receiving the user's response thereto;
  (g) detecting means located within the housing and coupled to the filtering means for detecting a second change in filtered voltage signal during the second time interval;
  (h) comparator located within the housing for comparing the first change in filtered voltage signal with the second change in filtered voltage signal and generating a comparison signal indicator of which change in filtered voltage signal is higher; and
  (i) indicating means located on a portion of the outside surface of the housing for providing to the user an indication of the comparison signal.

14. A method for determining which of two questions generates a greater psycho-physiological response in a user hearing the questions, comprising the steps of:
  (a) contacting adjacent fingers of the user to spaced electrodes;
  (b) applying a current across the electrodes and generating a measurable voltage signal related to the resistance of a section of the user's body extending between the electrodes;
  (c) signalling when the user should be asked a first question and allotting a time interval for the user's response;
  (d) detecting the change in voltage signal across the electrodes when the user responds to the first question during the first time interval;
  (e) filtering out components of the voltage signal outside of a preselected frequency range;
  (f) storing a first filtered voltage signal for the first time interval;
  (g) signalling when the player should be asked a second question and allotting a second time interval for the user's response;
  (h) detecting the change in voltage signal across the electrodes when the user responds to the second question during the second time interval;

(i) filtering out components of the voltage signal outside of a preselected frequency range;

(j) conditioning and then measuring a second filtered voltage signal for the second time interval;

(k) comparing the first filtered voltage signal with the second conditioned and filtered voltage signal and generating a comparison signal indicative of which of the two signals is greater; and (l) displaying to the user an indication of the comparison signal.

* * * * *